(12) United States Patent
Yang

(10) Patent No.: US 10,502,651 B2
(45) Date of Patent: Dec. 10, 2019

(54) CREATING A MINI ENVIRONMENT FOR GAS ANALYSIS

(71) Applicant: INFICON, Inc., East Syracuse, NY (US)

(72) Inventor: Chenglong Yang, Santa Clara, CA (US)

(73) Assignee: INFICON, INC., East Syracuse, NY (US)

( * ) Notice: Subject to any disclaimer, the term of this patent is extended or adjusted under 35 U.S.C. 154(b) by 328 days.

(21) Appl. No.: 15/285,627

(22) Filed: Oct. 5, 2016

(65) Prior Publication Data
US 2017/0097273 A1 Apr. 6, 2017

Related U.S. Application Data

(60) Provisional application No. 62/237,242, filed on Oct. 5, 2015.

(51) Int. Cl.
G01M 3/16 (2006.01)
G01M 3/38 (2006.01)
H01L 21/67 (2006.01)
H01L 21/66 (2006.01)
G01M 3/32 (2006.01)
G01N 21/71 (2006.01)
G01N 21/62 (2006.01)

(52) U.S. Cl.
CPC ............ G01M 3/16 (2013.01); G01M 3/3236 (2013.01); G01M 3/38 (2013.01); H01L 21/67028 (2013.01); H01L 21/67069 (2013.01); H01L 21/67253 (2013.01); H01L 21/67288 (2013.01); H01L 22/26 (2013.01); G01N 21/62 (2013.01); G01N 21/718 (2013.01)

(58) Field of Classification Search
CPC ........ G01M 3/16; G01M 3/3236; G01M 3/38; H01L 21/67288; H01L 22/26; H01L 21/67253; H01L 21/67069; H01L 21/67028; G01N 21/62; G01N 21/718
See application file for complete search history.

(56) References Cited

U.S. PATENT DOCUMENTS

| 4,609,426 A | * | 9/1986 | Ogawa | G01N 21/62 156/345.24 |
| 6,592,817 B1 | * | 7/2003 | Tsai | C23C 16/4412 422/505 |
| 2011/0222058 A1 | * | 9/2011 | Kim | G01J 3/443 356/316 |

* cited by examiner

Primary Examiner — Xin Y Zhong
(74) Attorney, Agent, or Firm — Barclay Damon LLP

(57) ABSTRACT

Systems and methods for in-situ leak detection and endpoint detection of wafer dry etch or chamber clean in chambers, e.g., vacuum chambers used in semiconductor processing. A mini environment is created and a sensor, such as an SPOES sensor, can be used in the mini-environment to perform leak detection.

26 Claims, 14 Drawing Sheets

CREATING A MINI ENVIRONMENT FOR GAS ANALYSIS

CROSS-REFERENCE TO RELATED APPLICATION

This application claims the benefit and priority of U.S. Patent application Ser. No. 62/237,242, filed Oct. 5, 2015, and entitled CREATING A MINI ENVIRONMENT FOR VACUUM CHAMBER LEAK DETECTION, the entirety of which is incorporated herein by reference.

FIELD OF THE INVENTION

The present application relates to in-situ leak detection and endpoint detection of wafer dry etch or chamber clean in chambers, e.g., vacuum chambers used in semiconductor processing.

BACKGROUND OF THE INVENTION

The process of making semiconductors, e.g., integrated-circuit transistors, involves numerous processes carried out under very low pressures. These pressures are maintained in what are commonly referred to as "vacuum chambers." In general, a vacuum chamber is an enclosure connected to a pumping system, e.g., one including a cryo pump or turbo pump. The pumping system maintains low or extremely low pressures, e.g., $10^{-8}$ Torr for a base pressure, and certain pressure, e.g., 5 mTorr during processing. The pumping system can optionally maintain specified concentrations of selected gasses in the chamber. An example of a cluster tool using chambers is the ENDURA physical vapor deposition (PVD) machine made by APPLIED MATERIALS. For example, PVD processes for depositing Cu and Ta(N) require high vacuum, e.g., ~5 mTorr. Throughout this disclosure, "vacuum" refers to pressures much lower than atmospheric (1 atm=760 Torr), e.g., <20 Torr.

The health of the vacuum system can be monitored in a variety of ways. For example, the pressure in the chamber can be plotted over time. Pressure increase can result from outgassing from moisture or other materials in the chamber, e.g., materials such as hydrocarbons coating the surface of the chamber or process kits. Pressure increase can also result from leaks between the chamber and the outside atmosphere, or between the chamber and its pumping or other components. For example, a leak in a cutoff valve can leak process gases, e.g., $N_2$ or Ar, into the chamber.

Since a 300 mm wafer can cost thousands of dollars, early detection of failures, i.e., leaks, can greatly improve the economic viability of a fab. Various in-situ chamber leak detection methods have been developed. For example, residual gas analyzers (RGAs) have been used to test chambers. RGAs perform mass spectroscopy on molecules in chambers to determine the composition of those molecules or their partial pressures. However, RGA equipment is bulky and expensive and the operating lifetime of the equipment is too low to apply it to every process chamber. Alternatively, oxygen ($O_2$) sensors have been used with some process chambers, such as Rapid Thermal Processing (RTP) chambers, for leak detection. However, the sensitivity of oxygen sensors is too poor for process chambers operating at low pressures.

Plasma assisted optical emission spectroscopy (SPOES) is suitable due to its low cost, small size, and long term stability. However, plasma OES is subject to a variety of disadvantages, such as a narrow operating pressure range. For example, some SPOES sensors have an operating pressure in the range of 10 mtorr to 1 torr, which pressure range is too low to maintain the plasma. Additionally, the sensitivity of the SPOES sensor varies for various gases. For example, the SPOES sensor is more sensitive for detecting nitrogen ($N_2$) compared to oxygen ($O_2$). In some SPOES sensors, the detection limit for nitrogen in 100 mTorr argon (Ar) is about 1 parts-per-million (ppm) while the detection limit for oxygen is greater than 100 ppm. Further, SPOES sensors are subject to interference from background gases, residual process gases, by-product gases, and other chambers.

As used herein, "measuring a chamber" can include measuring the pressure in a chamber, partial pressures of various gasses, or composition of the atmosphere in a chamber; or testing for or detecting leaks.

BRIEF DESCRIPTION OF THE INVENTION

According to various aspects, there are provided systems and methods of detecting process chamber leaks. A mini environment can be created in order to test for leaks. A sensor, such as an SPOES sensor, can be used in the mini-environment to perform leak detection.

In one embodiment, a vacuum system is described. The vacuum system includes a process chamber and a foreline coupled to the process chamber. A sensor manifold is coupled to the foreline and an assistant gas supply line is coupled to the sensor manifold. A sensor is coupled to the sensor manifold. The foreline is configured to flow a testing sample from the process chamber into the sensor manifold. The assistant gas supply line is configured to flow an assistant gas into the sensor manifold. The testing sample and the assistant gas form a mini environment in the sensor manifold.

In another embodiment, a sensor system for a vacuum chamber is described. The sensor system includes a sensor manifold and a sensor coupled to the sensor manifold. The sensor is configured to test for leaks in the vacuum chamber. An assistant gas supply line is coupled to the sensor manifold. The assistant gas supply line is configured to supply an assistant gas to the sensor manifold. The sensor manifold is configured to be coupled to a deposition chamber foreline.

In yet another embodiment, a method for leak detection of a vacuum process chamber is described. A foreline and a sensor system are coupled to the vacuum process chamber. The sensor system includes a sensor manifold coupled to the foreline, a sensor coupled to the sensor manifold, and an assistant gas supply line coupled to the sensor manifold. The method includes flowing a testing gas sample into the sensor manifold and flowing an assistant gas into the sensor manifold to create a mini environment. The method further includes activating the sensor and testing, with the sensor, the mini environment to identify a leak in the vacuum process chamber.

This brief description of the invention is intended only to provide a brief overview of subject matter disclosed herein according to one or more illustrative embodiments, and does not serve as a guide to interpreting the claims or to define or limit the scope of the invention, which is defined only by the appended claims. This brief description is provided to introduce an illustrative selection of concepts in a simplified form that are further described below in the detailed description. This brief description is not intended to identify key features or essential features of the claimed subject matter, nor is it intended to be used as an aid in determining the scope of the claimed subject matter. The claimed subject matter is not limited to implementations that solve any or all disadvantages noted in the background.

BRIEF DESCRIPTION OF THE DRAWINGS

The above and other objects, features, and advantages of the present invention will become more apparent when taken in conjunction with the following description and drawings wherein identical reference numerals have been used, where possible, to designate identical features that are common to the figures, and wherein.

The attached drawings are for purposes of illustration and are not necessarily to scale.

DETAILED DESCRIPTION OF THE INVENTION

In the following description, some aspects will be described in terms that would ordinarily be implemented as software programs. Those skilled in the art will readily recognize that the equivalent of such software can also be constructed in hardware, firmware, or micro-code. Because data manipulation algorithms and systems are well known, the present description will be directed in particular to algorithms and systems forming part of, or cooperating more directly with, systems and methods described herein. Other aspects of such algorithms and systems, and hardware or software for producing and otherwise processing the signals involved therewith, not specifically shown or described herein, are selected from such systems, algorithms, components, and elements known in the art. Given the systems and methods as described herein, software not specifically shown, suggested, or described herein that is useful for implementation of any aspect is conventional and within the ordinary skill in such arts.

Figure 1:
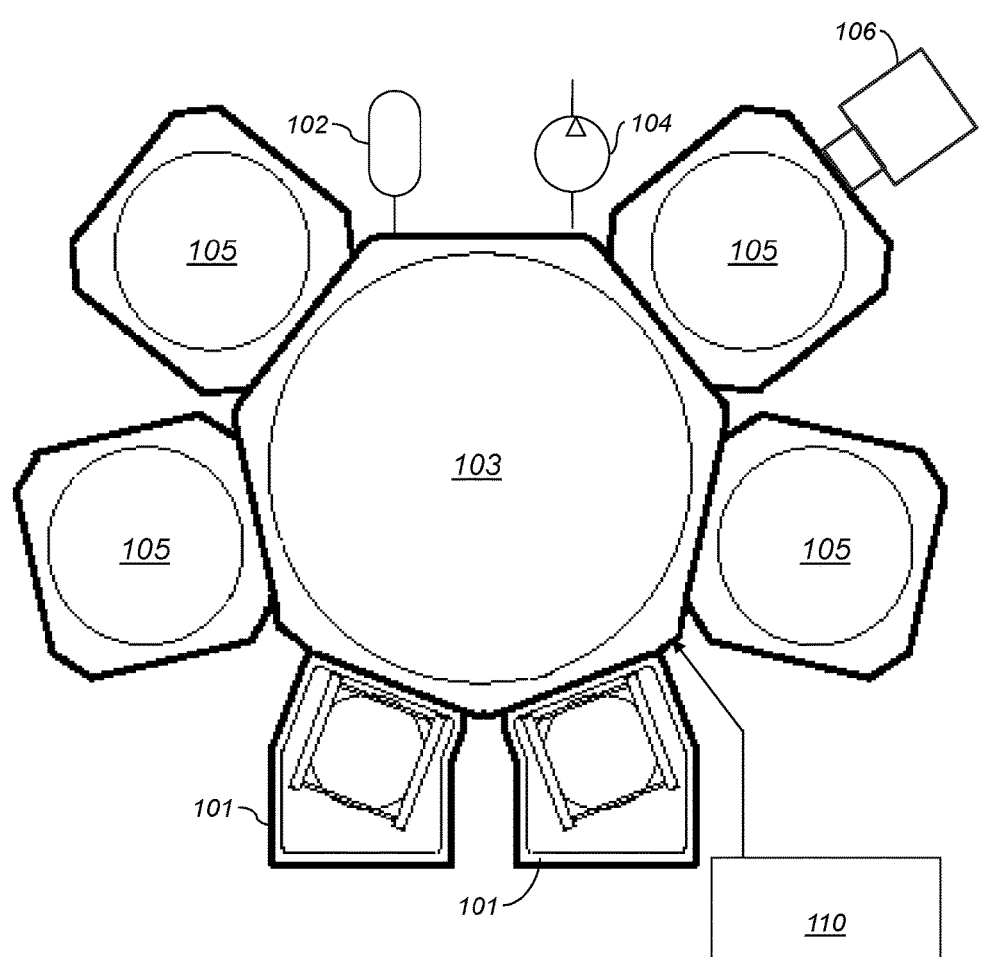
FIG. 1 shows an example of a cluster tool.

FIG. 1 shows an example of a cluster tool having two load-locks 101, one transfer chamber 103, and four process chambers 105. Silicon wafers or other substrates (all referred to herein as "wafers") pass into and out of the tool through the load-locks, which are chambers. Various operations are performed on the wafers in the process chambers 105. Wafers are transferred between these chambers by robotic arms or other actuators in the transfer chamber 103. The transfer chamber 103 is kept at an extremely low pressure, e.g. less than $10^{-7}$ Torr, by a pump 102, e.g., a vacuum pump. A sensor 106, such as a plasma assisted OES (SPOES) sensor, is coupled to at least one chamber in order to perform in-situ leak detection. In an example, an SPOES 106 is coupled to each process chamber 105 in order to measure all the process chambers 105, as described herein. Various devices can be used for the SPOES sensor 106. For example, an INFICON Quantus LP100 can measure atmospheres at pressures between 10 mtorr and 1 torr.

An Equipment Controller 110 controls the operation of the cluster tool and its chambers, pump 102, and gas supply 104 to carry out a recipe. A "recipe" is a sequence of wafer movements and operations to be performed when a wafer is in a specific chamber. Examples of recipes are given in Herrmann et al, "Evaluating the Impact of Process Changes on Cluster Tool Performance", *IEEE Transactions on Semiconductor Manufacturing* (ISSN 0894-6507), vol. 13, no. 2, May 2000, incorporated herein by reference. The controller 110 can include a microprocessor, microcontroller, programmable-logic device (PLD), programmable logic array (PLA), programmable array logic (PAL), field-programmable gate array (FPGA), application-specific integrated circuit (ASIC), or other computing or logic device programmed, wired, or configured to perform functions described herein. A sensor controller (not shown), such as a SPOES sensor Controller, can be connected to the equipment controller 110. In various aspects, the equipment controller 110 and the sensor controller are two logic modules, subroutines, threads, or other processing components of a single controller.

The system includes a mainframe assembly (loadlocks 101, transfer chamber 103, process chambers 105) and an associated set of remote support equipment (RF power supplies, vacuum pumps, heat exchangers, computers). For example, various aspects can be used with an APPLIED MATERIALS CENTURA, a LAM RESEARCH 2300, a TOKYO ELECTRON TELIUS, or other tools. Process chambers 105 can be configured for etching, chemical vapor deposition (CVD), thermal processing, or other processes. Gas supply 104 supplies desired atmospheric components to the transfer chamber 103 while pump 102 is operating. In an example, gas supply 104 supplies argon (Ar) gas or nitrogen gas ($N_2$) so that the transfer chamber 103 is filled with low-pressure argon or $N_2$ instead of with air. Tools can include 3-4 process chambers 105 around a single central chamber pumped down to ~10 mTorr. In various aspects, during wafer transfer, all chambers 105 involved in the transfer, or all chambers 105 in the tool, are pumped down with gas flow to set the composition and pressure of the atmosphere in the chambers. During tool idle, gas can be pumped through the chambers 105 to maintain a selected atmosphere.

In an example, SPOES sensors 106 can be used to check for leaks in attached chambers 105 in sequence. Leak checking and other measurements can be performed before wafer processing, during wafer processing, after wafer processing, or while the tool is in idle, clean mode, or purge. In various aspects, described further below, leak-checking is done by forming a mini environment, which is particularly suited to operation of the SPOES sensor 106, in the chamber 105 undergoing testing. The mini environment can be formed by changing the pressure and/or the composition of the environment within the chamber 105.

Figure 2:
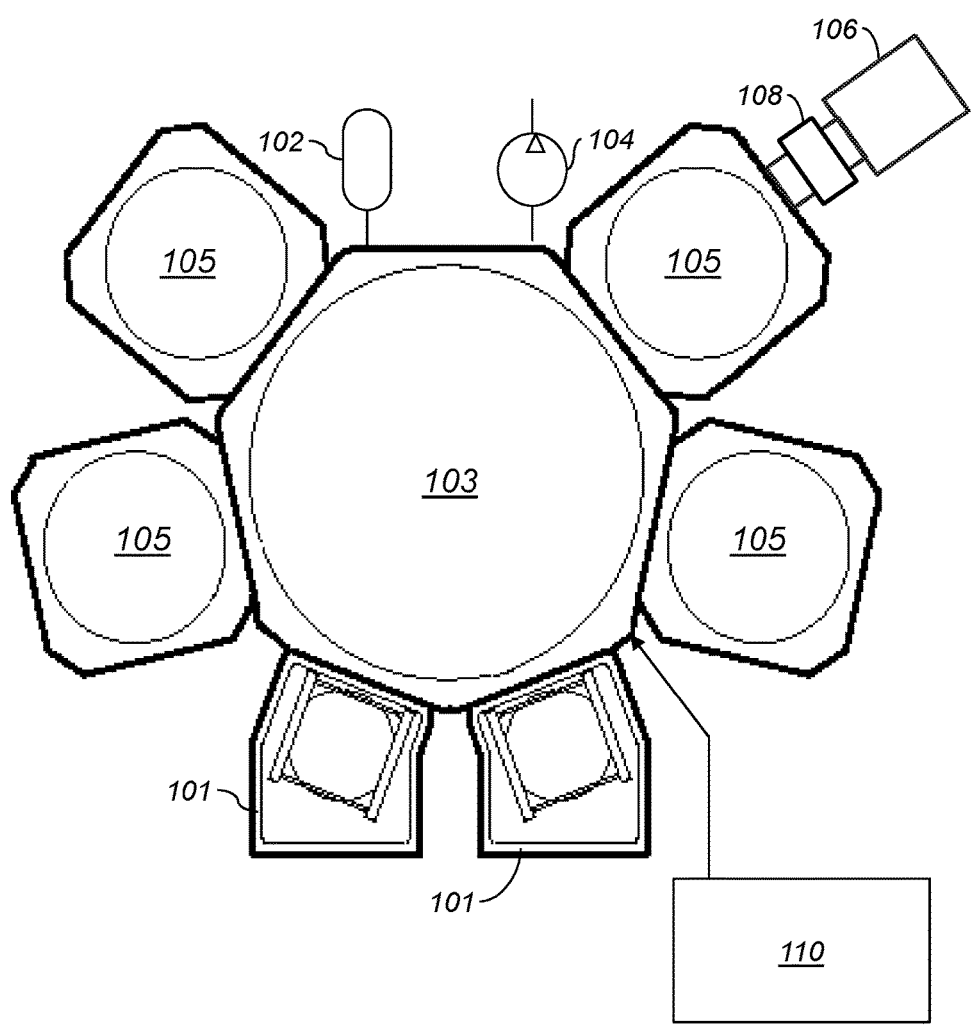
FIG. 2 shows another example of a cluster tool.

FIG. 2 shows another example of a cluster tool. Similar to the cluster tool illustrated in FIG. 1, this cluster tool has two load-locks 101, one transfer chamber 103, and four process chambers 105. In addition, the cluster tool includes an isolation valve 108 positioned between the process chamber 105 and the sensor 106. The isolation valve 108 is positioned to isolate the sensor 106 from the reactive gases in the process chamber 105 when leak detection testing is not actively occurring, thus increasing the life of the sensor 106. Additionally, operation of the isolation valve 108 can be used to control when the sensor 108 is activated to test for a chamber leak.

In an example, operation of the isolation valve 108 is controlled by a sensor controller (not shown), such as with a relay. In another example, the isolation valve 108 is controlled by the equipment controller 110, such as by the pneumatic gas from the process chamber. Operation of the isolation valve 108 requires communication and/or integration between the equipment controller 110 and the sensor controller. In an example, this communication can be enacted through hardware I/O or SEMI equipment communications standard (SECS) communication.

Figure 3:
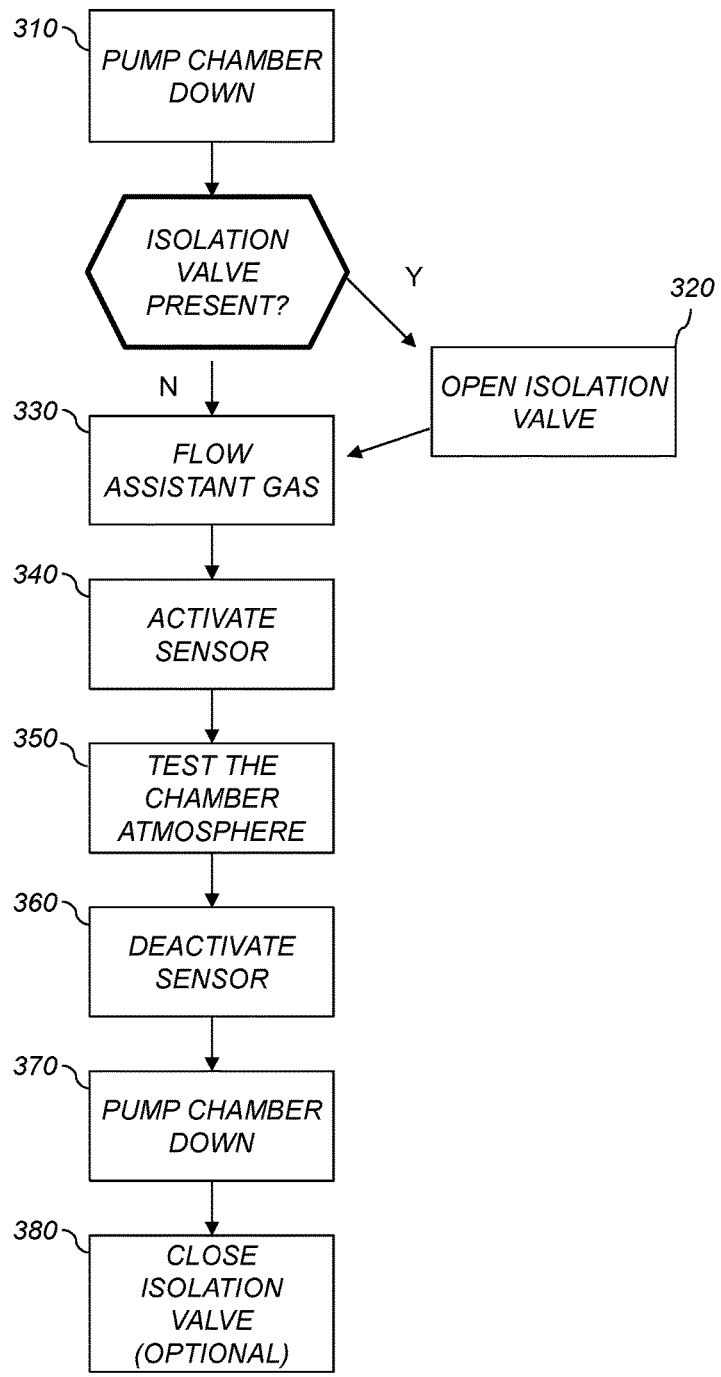
FIG. 3 is a flow diagram illustrating an example of a method of in-situ leak detection employed during non-processing times.

FIG. 3 shows an example of a method of measuring chambers. The blocks in FIG. 3 can be performed in the order shown, or in any other suitable order. Blocks can be skipped and, in various examples, blocks can be performed simultaneously. In an example, the method can be carried out during non-processing times, such as before processing, after processing, or between processing steps.

In block 310, a process chamber 105 (FIGS. 1, 2, 7), to which a sensor 106 is coupled, is pumped down to obtain a stable base pressure. The process chamber 105 can be any type, such as a PVD, Metal Organic Chemical Vapor Deposition (MOCVD), CVD or Atomic Layer Deposition (ALD) deposition chamber. In an example, the pump 102 can operate continuously, in which case block 310 includes waiting for the base pressure to be reached. If an isolation valve 108 is present between the process chamber 105 and the sensor 106, at block 320 the isolation valve is opened before the assistant gas flows into the process chamber 105 at block 330. A gas suitable for the sensor 106 is selected as the assistant gas. The assistant gas is flowed into the process chamber 105 until a suitable pressure for operation of the sensor 106 is reached in the process chamber 105. In an example, Argon gas is flowed into the system to create a pressure of about 100 mTorr (50~500 mT) in the process chamber 105, which environment is particularly suitable for operation of the SPOES sensor 106. Creation of the mini environment occurs over about 1-20 seconds.

At block 340, the plasma of the sensor 106 is activated and, at block 350, the sensor 106 tests the chamber atmosphere in the process chamber 105 to detect any chamber leaks. At block 360, the plasma is deactivated of the sensor 106 and, at block 370, the process chamber 105 is pumped down. If the system includes an isolation valve, at block 380, the isolation valve is closed. Following leak detection, normal operation of the process chamber 105 can resume.

Figure 4:
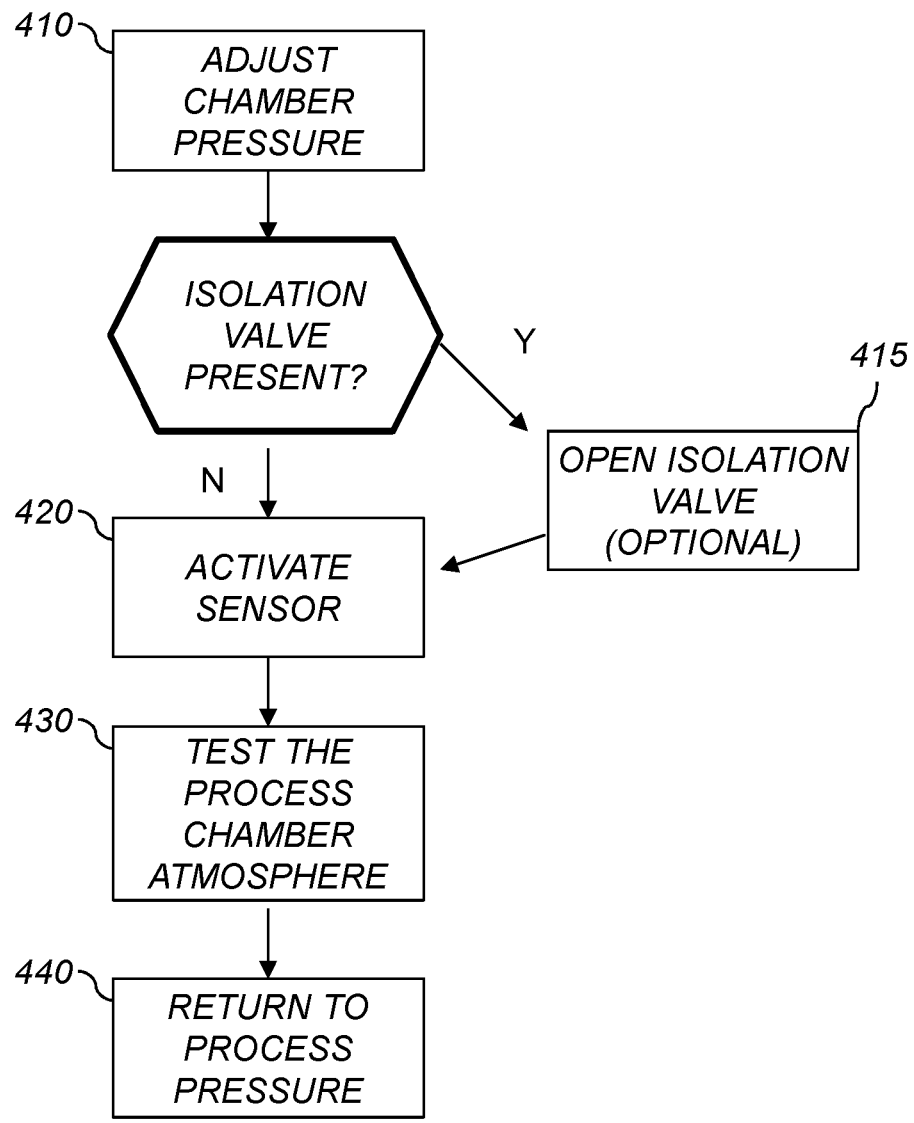
FIG. 4 is a flow diagram illustrating an example of a method of in-situ leak detection employed during processing.

FIG. 4 is a flow diagram illustrating another method of performing in-situ leak detection. This method can be employed during wafer processing when the processing gases are suitable for operation of the sensor 106. This method can be employed be a suitable system, such as the cluster tools illustrated in FIGS. 1, 2, and 7.

At block 410, the chamber pressure is adjusted until the testing pressure is reached. For example, gas can be added to or released from the process chamber 105 until the testing pressure is reached. In an example, the testing pressure is about 500 mTorr. If an isolation valve is present between the process chamber 105 and the sensor 106, the isolation valve can be opened at block 415 prior to activation of the sensor at block 420. At block 430, the chamber atmosphere is tested to identify any leaks present in the process chamber 105. At block 440, the chamber pressure is returned to the processing pressure and wafer processing continues. If an isolation valve is present, the valve is closed prior to returning to the process pressure.

Figure 5:
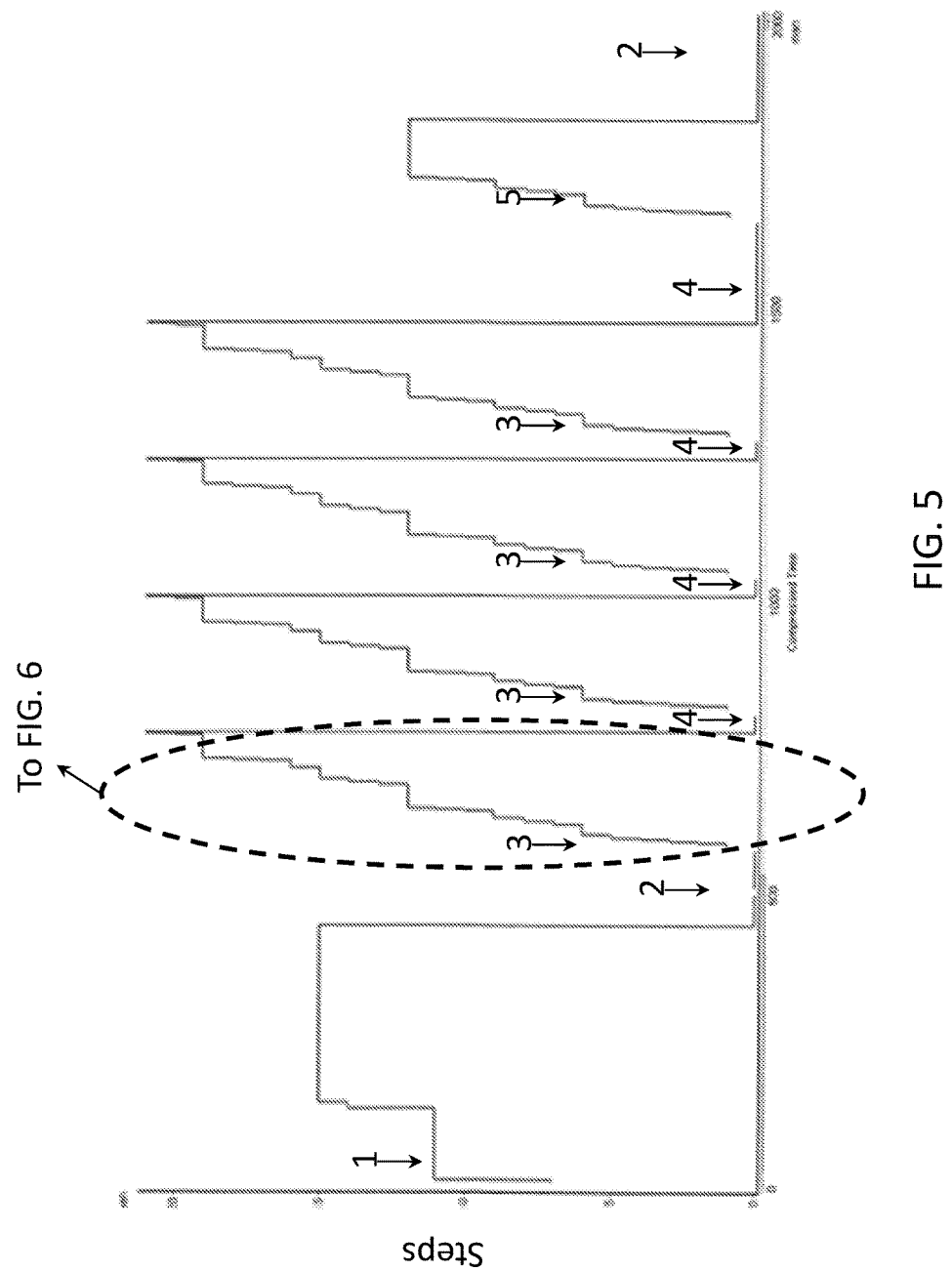
FIG. 5 is an illustration of example process sequences.
Figure 6:
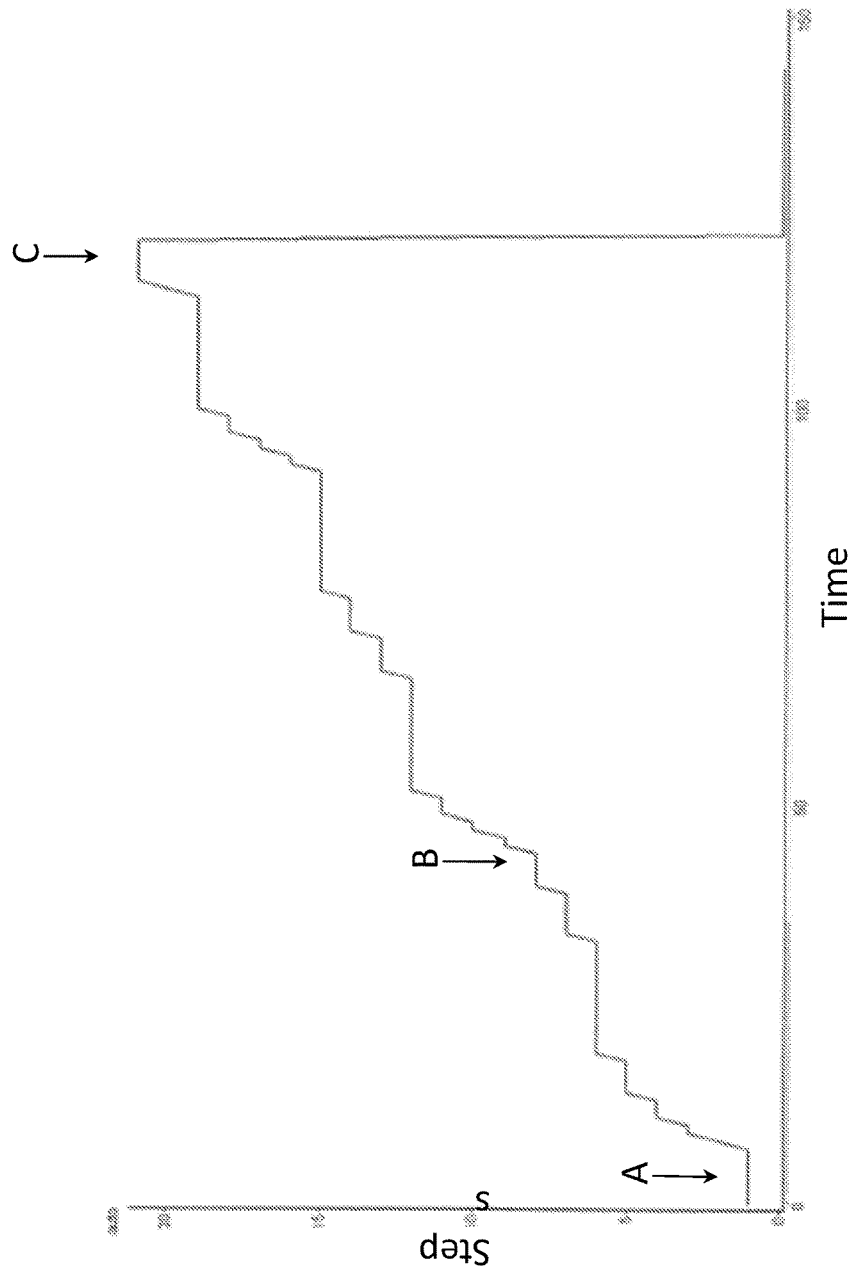
FIG. 6 of a wafer processing peak from FIG. 5.

FIG. 5 is a diagram illustrating the operating sequences of a cluster tool, such as a CVD tool. The sequences include the following non-processing states: purge state 1, idle 2, and clean 5. Additionally, the sequences include the following processing, e.g., deposition, states: during wafer 3 and inter-wafer 4. As illustrated by FIG. 6, which is an enlarged view of one of the peaks indicating a deposition process, during wafer 3 can include before wafer processing A, during wafer processing B, and after wafer processing C.

A suitable mini-environment can be created when the chamber is any of these processing and non-processing states, thus enabling in-situ leak detection to occur during processing and non-processing times. For example, the method illustrated in FIG. 3 can be employed when the tool is in the purge state 1, idle state 2, clean state 5 and inter-wafer state 4 and the method illustrated in FIG. 4 can be employed when the tool is in the during wafer state 3.

Figure 7:
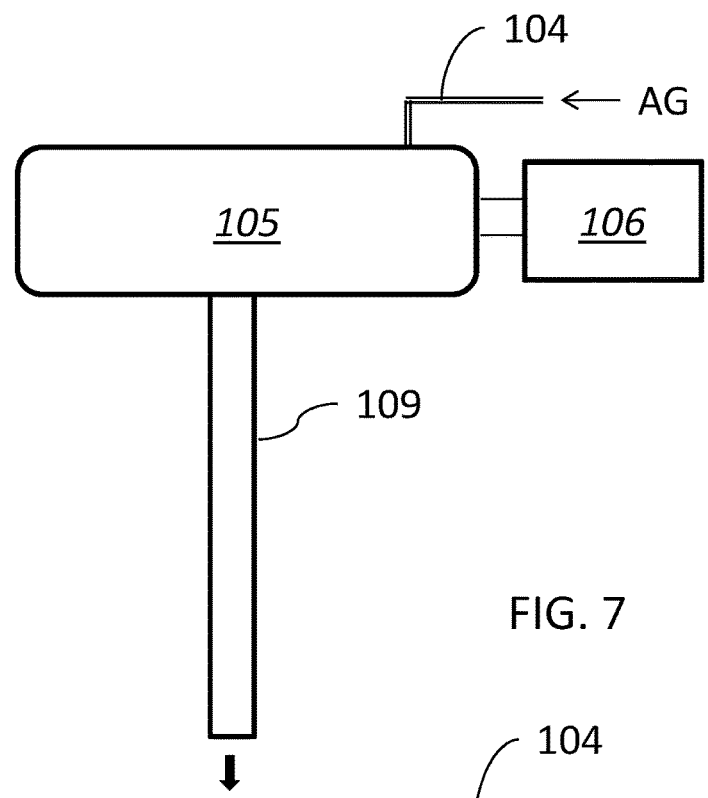
FIG. 7 is an illustration of an example of a sensor system.

Referring to FIG. 7 and as discussed above with regard to FIGS. 1 and 2, gas can be supplied to a process chamber 105 via the gas supply 104. Gas is removed from the process chamber 105 via the foreline. A sensor 106, such as an SPOES sensor, is coupled to the process chamber 105. In operation, assistant gas AG if flowed into the process chamber 105 and the sensor 106 performs leak detection in the process chamber 105. Following testing, the assistant gas AG is flowed out of the chamber through the foreline 109.

Figure 8:
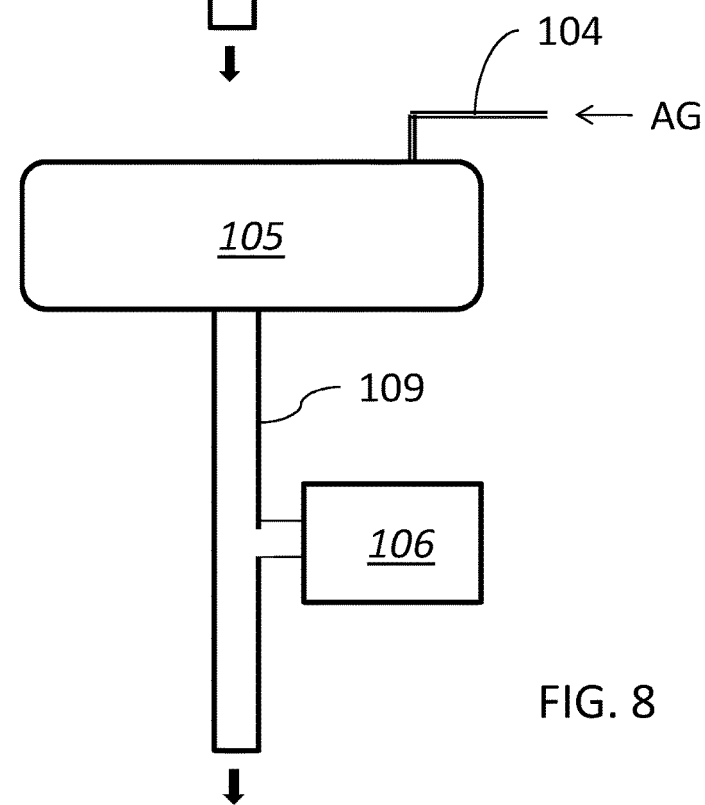
FIG. 8 is an illustration of another example of a sensor system.
Figure 9:
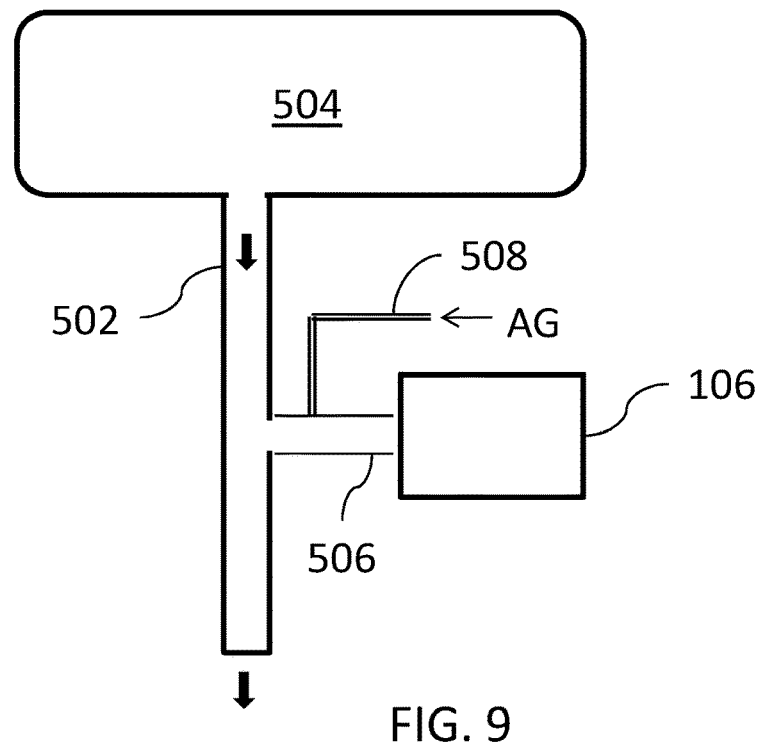
FIG. 9 is an illustration of another example of a sensor system.

Referring to FIG. 8, in another embodiment, the sensor 106 is coupled to the foreline 109. In operation, assistant gas AG flows into the process chamber 105 via the gas supply line 104 and out of the process chamber 105 through the foreline 109. As the assistant gas AG flows through the foreline 109, a portion of the assistant gas is diverted to the sensor 106 for testing.

Referring to FIGS. 9-17, in another embodiment, the mini-environment is created in the system outside the process chamber so that leak detection can be conducted outside said process chamber. In an embodiment, illustrated by FIG. 9, a foreline 502 is coupled to the process chamber 504 for removing gas from the process chamber 504. A sensor, such as an SPOES sensor 106 is coupled to the foreline 502 via a sensor manifold 506. In this embodiment, an assistant gas supply line 508 is coupled to the sensor manifold 506. As gas exits the process chamber 504 through the foreline 502, at least a portion of the gas travels through the sensor manifold 506 to the sensor 106. In this embodiment, the sensor manifold 506 is a simple, unidirectional manifold. In another embodiment, illustrated by FIGS. 15-17, a sensor manifold 507 includes an inlet portion 510 and an outlet portion 512.

Referring back to FIG. 9, an assistant gas AG is injected through the assistant gas supply line 508 into the sensor manifold 506 to form the mini environment, which is particularly suited to operation of the SPOES sensor 106, in the sensor manifold 506. The mini environment can be formed by changing the pressure and/or the composition of the environment within the sensor manifold 506. By forming and sampling the mini environment outside the process chamber 504 with the addition of the assistant gas, a suitable gas chemistry or gas pressure can be created to meet the requirements of the plasma sensor operating conditions including chemistry and pressure. In addition, the clean endpoint detection of the process chamber 504 can be performed. In addition, by conducting leak detection and other gas analysis outside the process chamber, such analysis is not restricted by the timing of the cycles in the process chamber 504 and can rather be conducted at any time.

Figure 10:
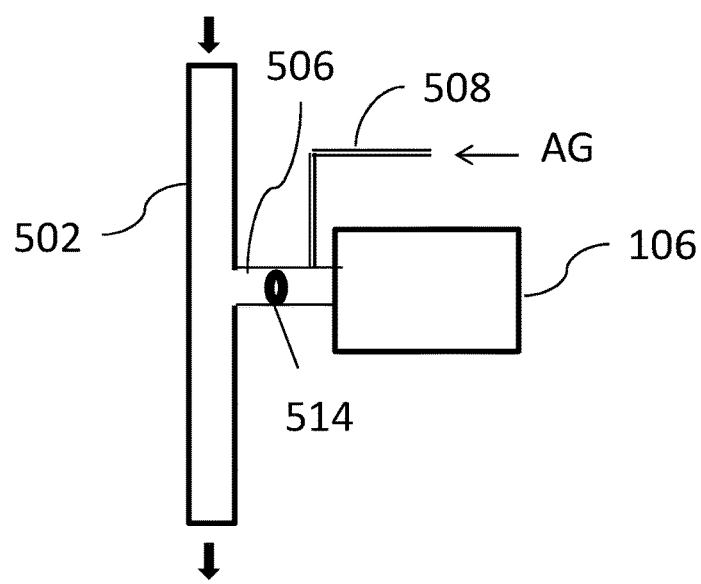
FIG. 10 is an illustration of another example of a sensor system.
Figure 11:
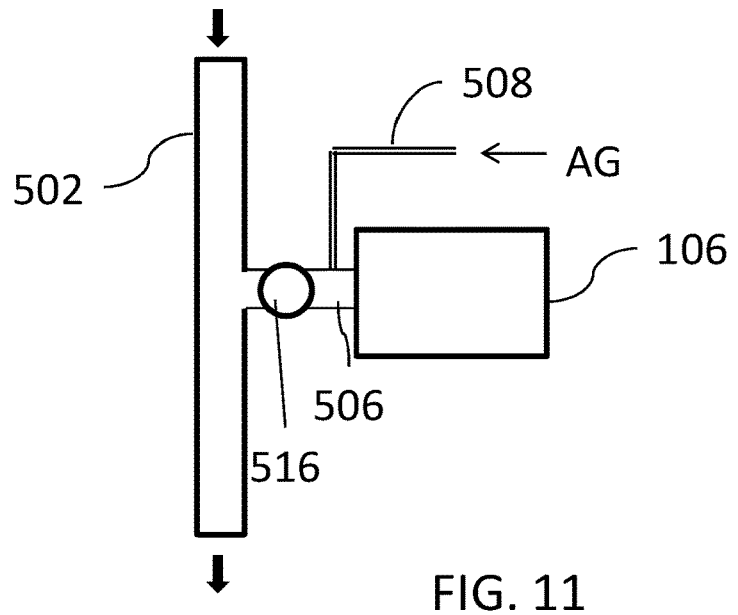
FIG. 11 is an illustration of another example of a sensor system.
Figure 12:
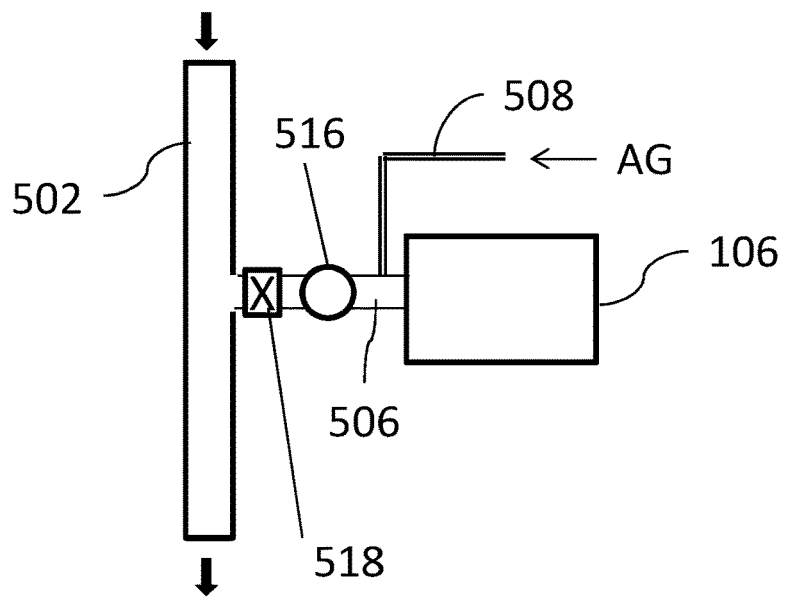
FIG. 12 is an illustration of another example of a sensor system.
Figure 13:
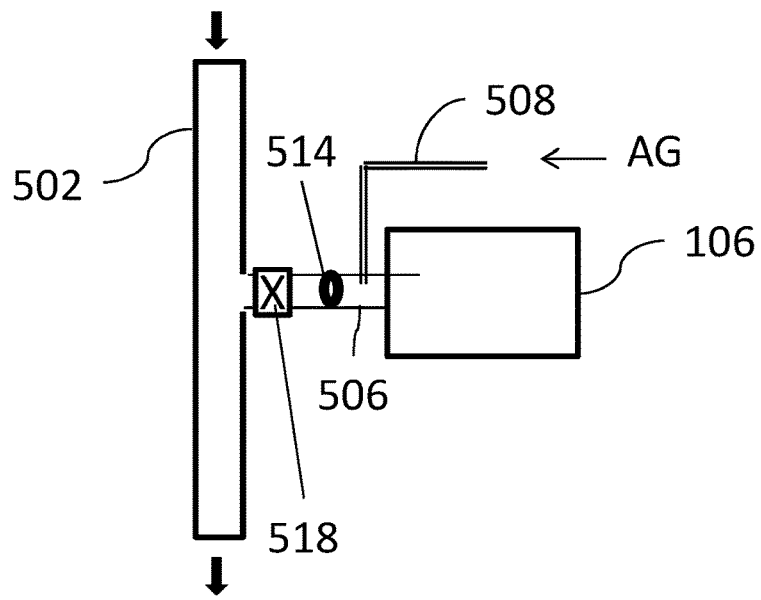
FIG. 13 is an illustration of another example of a sensor system.
Figure 14:
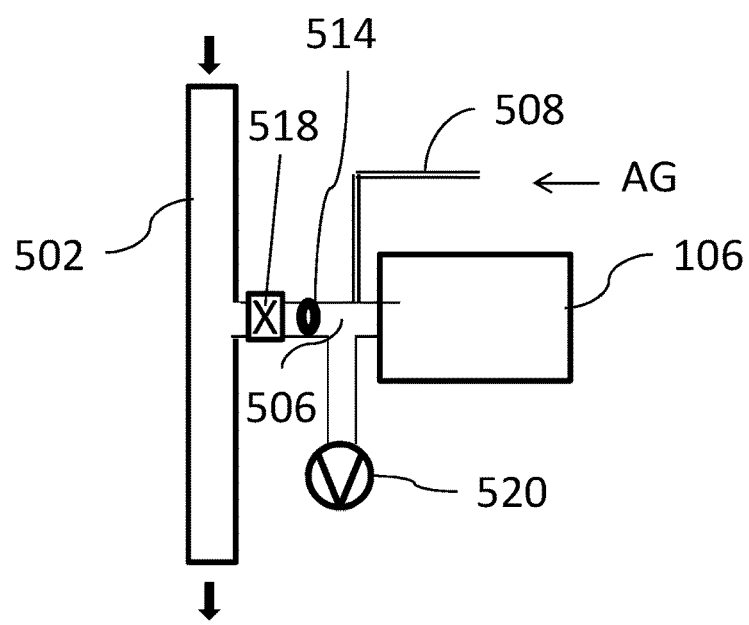
FIG. 14 is an illustration of another example of a sensor system.
Figure 15:
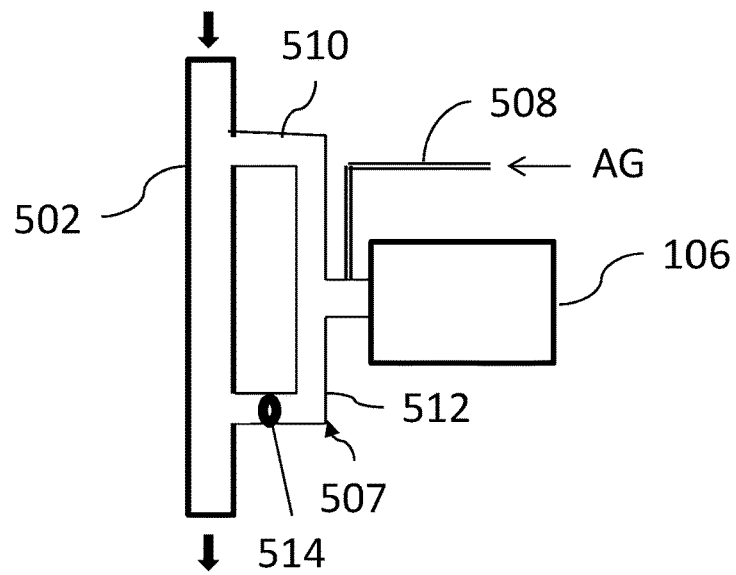
FIG. 15 is an illustration of another example of a sensor system.
Figure 16:
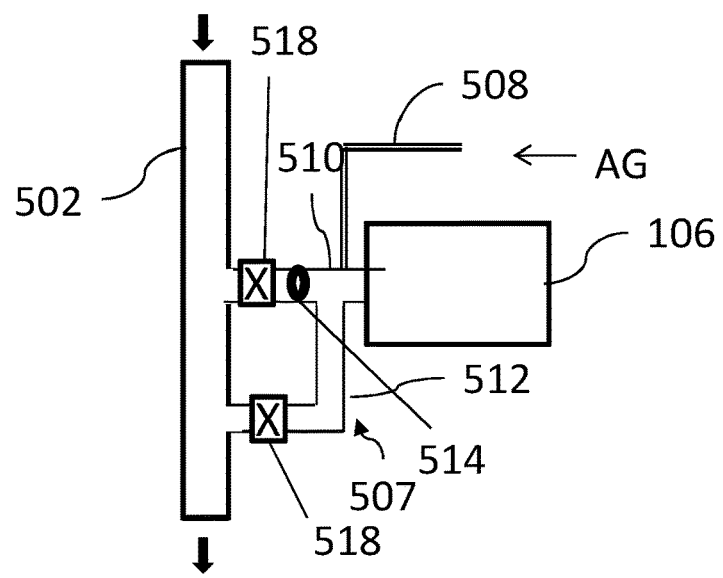
FIG. 16 is an illustration of another example of a sensor system.
Figure 17:
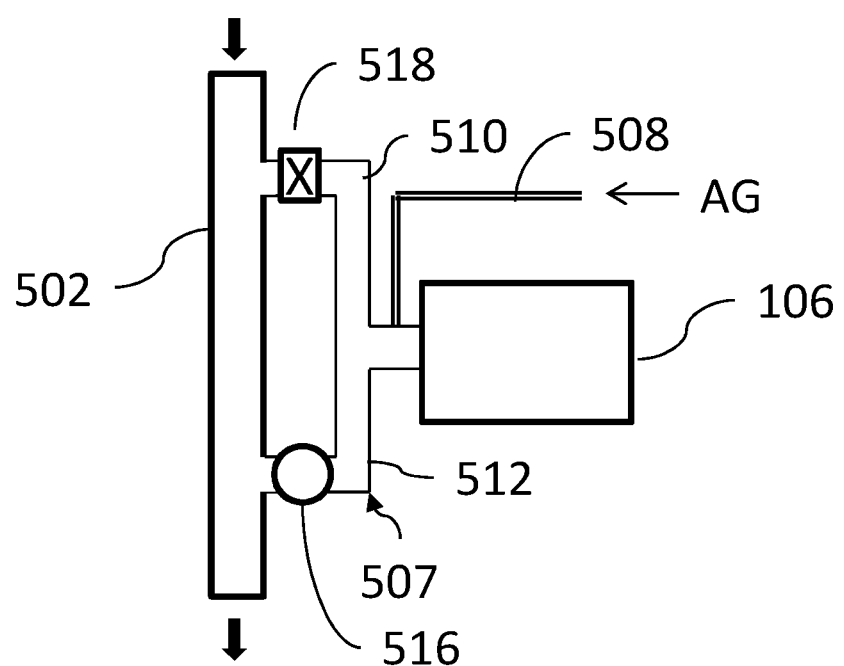
FIG. 17 is an illustration of another example of a sensor system.

As illustrated by FIGS. 10-17, various control elements, such as a restriction orifices 514, pressure controllers 516, pumps 520, and isolation valves 518, can be used to control the flow of gas, and thus pressure, in the sensor manifold 506. For example and as illustrated in FIG. 10, a restriction orifice 514 can be positioned within the sensor manifold 506 to control movement of gases from the foreline 502 into the sensor manifold 506 to create a pressure differential between the foreline 502 and the sensor manifold 506, and thus control the pressure in the sensor manifold 506. In another example, illustrated in FIG. 11, a pressure controller 516 is positioned in the sensor manifold 506. In another example, illustrated by FIGS. 12-14, the sensor manifold 506 can include a plurality of control elements. For example, FIG. 12 illustrates a sensor manifold 506 including a pressure controller 516 and an isolation valve 518. FIG. 13 illustrates a sensor manifold 506 including an isolation valve 518 and a restriction orifice 514. FIG. 14 illustrates a pressure manifold 506 with an isolation valve 518, a restriction orifice 514, and a pump 520. In this example, the pump 520 is used to create the pressure differential between the sampling pressure and the sensor pressure and allows the sensor pressure to be in the range of the sensor operating pressure.

As discussed above and illustrated by FIGS. 15-17, a sensor manifold 507 can include an inlet portion 510 and an outlet portion 512. The sensor manifold 507 can include one or more control elements, placed in the inlet portion 510, the outlet portion 512, or in both the inlet portion 510 and the outlet portion 512. For example, illustrated by FIG. 15, a restriction orifice 514 is positioned in the outlet portion 512. In another example, illustrated by FIG. 16, an isolation valve 518 and a restriction orifice 514 are positioned in the inlet portion 510 and a second isolation valve 518 is positioned in the outlet portion 512. In another example, illustrated by FIG. 17, an isolation valve 518 is positioned in the inlet portion 510 and a pressure controller 516 is positioned in the outlet portion 512.

Figure 18:
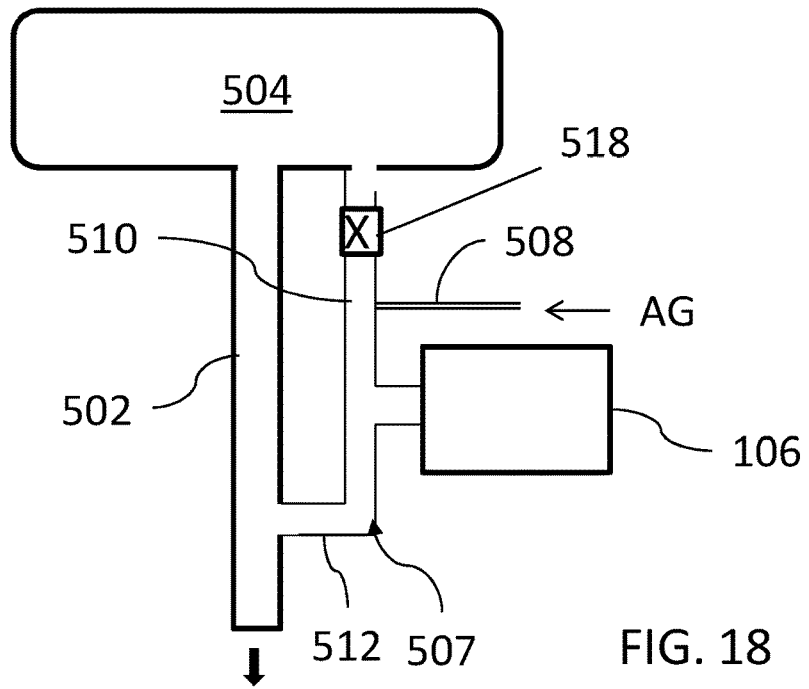
FIG. 18 is an illustration of another example of a sensor system.
Figure 19:
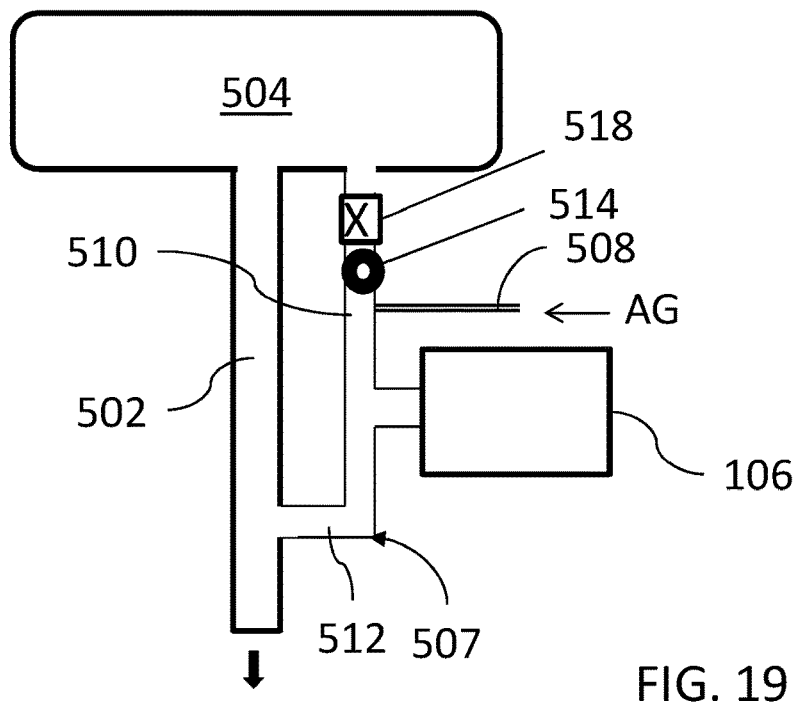
FIG. 19 is an illustration of another example of a sensor system.

In another embodiment, illustrated by FIGS. 18-19, a foreline 502 is coupled to the process chamber 504. The sensor manifold 507 has an inlet portion 510 and an outlet portion 512. In the illustrated embodiments, the inlet portion 510 of the sensor manifold 507 is coupled to the process chamber 504 and the outlet portion 512 of the sensor manifold 506 is coupled to the foreline 502. An assistant gas supply line 508 is coupled to the sensor manifold 507, upstream of the sensor 106. As illustrated, various control elements, such as an isolation valve 518 and a restriction orifice 514, can be coupled to the sensor manifold 507. In operation, gas flows from the process chamber 504 into the inlet portion 510 of the sensor manifold 507 and through the outlet portion 512 to the foreline 502. An assistant gas AG can be injected to the inlet portion 510 of the sensor manifold 507 via the assistant gas supply line 508. The sensor 106 can test the gas present in the sensor manifold 507.

Figure 20:
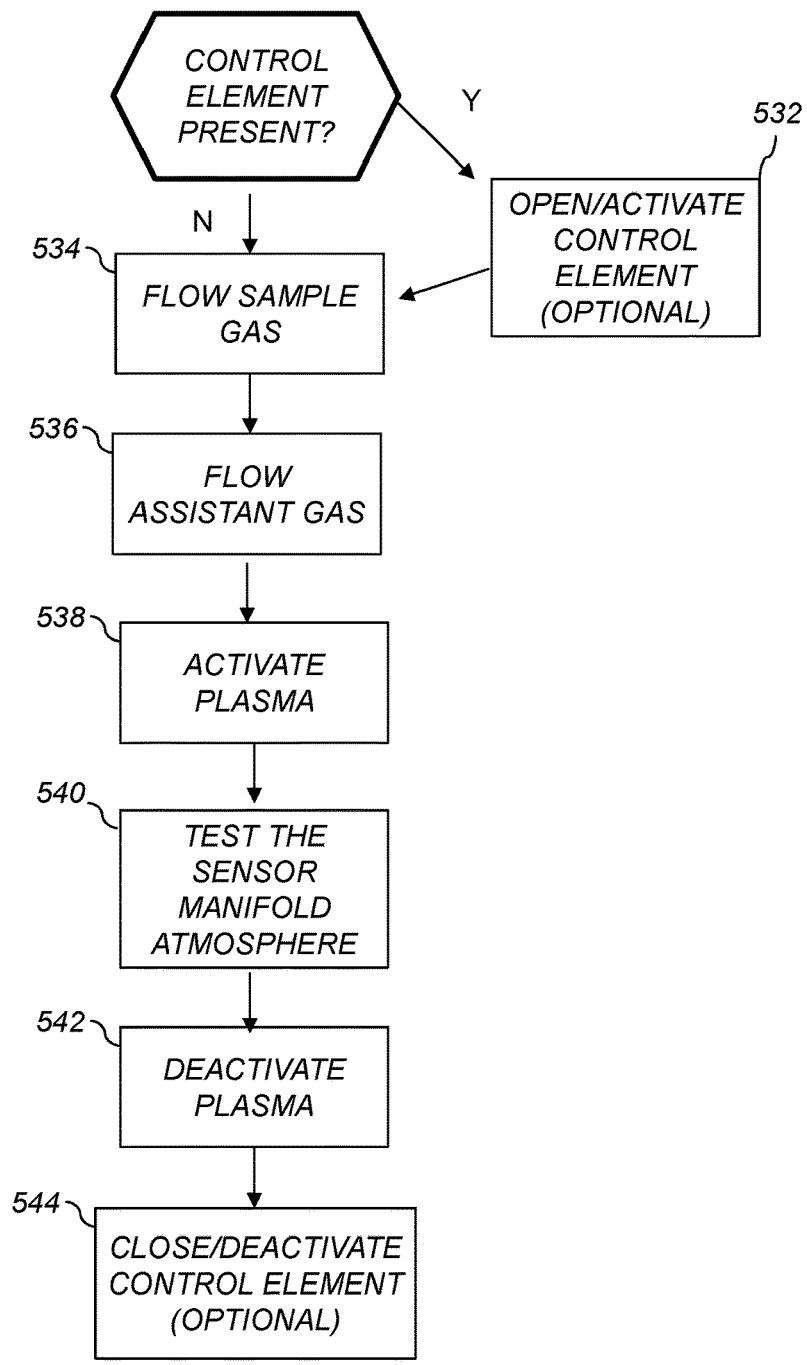
FIG. 20 is a flow diagram illustrating an example of a method of leak detection in a sensor manifold.

FIG. 20 shows an example of a method of measuring the sensor manifold in a system, such as one of the systems illustrated in FIGS. 9-19. The blocks in FIG. 20 can be performed in the order shown, or in any other suitable order. Blocks can be skipped and, in various examples, blocks can be performed simultaneously. In an example, the method can be carried out during non-processing times, such as before processing, after processing, or between processing steps. In another embodiment, the method can be carried out during processing times.

If a control element 514, 516, 518, 520 is present in a sensor manifold 506, 507, at block 532 the control element 514, 516, 518, 520 is opened or activated. The control element 514, 516, 518, 520 can be any suitable type of control element, such as a restriction orifice 514, isolation valve 518, pressure controller 516, pump 520, or any other suitable type of control element. At block 534, the sample gas is flowed into the sensor manifold 506, 507. The sample gas can flow into the sensor manifold 506, 507 from the foreline 502 or directly from the process chamber 504. At block 536, an assistant gas AG is flowed into the sensor manifold 506, 507 from the assistant gas supply line 508. In an example, the gas is flowed into the sensor manifold 506, 507 until a suitable pressure and/or composition for operation of the sensor 106 is reached in the sensor manifold 506, 507.

At block 538, the plasma is activated and, at block 540, the sensor 106 tests the sensor manifold atmosphere to detect any chamber leaks. At block 542, the plasma is deactivated and the sample gas is allowed to flow out of the sensor manifold 506, 507 into the foreline 502. If the system includes a control element 514, 516, 518, 520, at block 544, the control element is closed or deactivated.

In one embodiment, the reaction gas for an assistant gas could be used to enhance the detection sensitivity. As an example, there is low sensitivity for plasma OES to detect $O_2$. However, adding the reaction gas of $N_2$ in the mini environment can form the NO in the plasma OES, which has a much higher sensitivity of detecting NO instead of $O_2$. The assistant gas could be one gas or a mixing of gases The invention is inclusive of combinations of the aspects described herein. References to "a particular aspect" and the like refer to features that are present in at least one aspect of the invention. Separate references to "an aspect" or "particular aspects" or the like do not necessarily refer to the same aspect or aspects; however, such aspects are not mutually exclusive, unless so indicated or as are readily apparent to one of skill in the art. The use of singular or plural in referring to "method" or "methods" and the like is not limiting. The word "or" is used in this disclosure in a non-exclusive sense, unless otherwise explicitly noted.

The invention has been described in detail with particular reference to certain preferred aspects thereof, but it will be understood that variations, combinations, and modifications can be effected by a person of ordinary skill in the art within the spirit and scope of the invention. Further, where exemplary embodiments are described with reference to a certain number of elements it will be understood that the exemplary embodiments can be practiced utilizing either less than or more than the certain number of elements.

The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A vacuum system, comprising:
a process chamber;
a foreline in fluid communication with the process chamber;
a sensor manifold coupled to the foreline;
a sensor coupled to the sensor manifold; and
a sensor assistant gas supply line coupled to the sensor manifold,
wherein the foreline is configured to effect a flow of a chamber gas from the process chamber into the sensor manifold,
wherein the sensor assistant gas supply line is configured to effect a flow of the sensor assistant gas into the sensor and,
wherein the sensor assistant gas is configured to augment the operation of the sensor by enabling the evaluation of pressure variations and amplifying the sensitivity of the sensor.

2. The vacuum system of claim 1, wherein the sensor assistant gas is configured to test for leaks in the process chamber.

3. The vacuum system of claim 1, wherein the sensor comprises a plasma assisted optical emission spectroscopy (SPOES) sensor.

4. The vacuum system of claim 1, further comprising a control element coupled to the sensor manifold and configured to control pressure in the sensor manifold.

5. The vacuum system of claim 4, wherein the control element comprises a restriction orifice, an isolation valve, a pressure controller, a pump, or a combination thereof.

6. The vacuum system of claim 1, wherein the sensor manifold comprises an inlet portion and an outlet portion, the outlet portion coupled to the foreline.

7. The vacuum system of claim 6, wherein the inlet portion is coupled to the foreline.

8. The vacuum system of claim 6, wherein the inlet portion is coupled to the process chamber.

9. The vacuum system of claim 1, wherein the sensor assistant gas is configured to test for leaks in the sensor.

10. The vacuum system of claim 1, wherein the sensor assistant gas is configured to test for changes in chemistry as a consequence of a sensor plasma produced by the sensor.

11. The vacuum system of claim 1 wherein the chamber and sensor assistant gases are combined to enable evaluation of: (i) changes in pressure within the pressure chamber (ii) changes in pressure within the sensor, and (iii) changes in the chemistry as a consequence of a sensor plasma produced by the sensor.

12. The vacuum system of claim 1 wherein the sensor assistant gas is $N_2$.

13. A sensor system for a vacuum chamber, comprising:
a sensor manifold;
a sensor coupled to the sensor manifold, the sensor configured to test for leaks in the vacuum chamber; and
a gas supply line coupled to the sensor manifold, the gas supply line configured to supply a sensor assistant gas to the sensor manifold for accessing the sensor,
wherein the sensor manifold is configured to be coupled to a chamber foreline,
wherein the foreline is configured to effect a flow of a chamber gas from the vacuum chamber into the sensor manifold,
wherein the gas supply line is configured to effect a flow of a sensor assistant gas into the sensor, and,
wherein the sensor assistant gas is configured to augment the operation of the sensor by enabling the evaluation of pressure variations and amplifying the sensitivity of the sensor.

14. The sensor system of claim 13, wherein the sensor comprises a plasma assisted optical emission spectroscopy (SPOES) sensor.

15. The sensor system of claim 13 wherein the sensor assistant gas is $N_2$.

16. A method for detecting leaks in a vacuum chamber system including sensor system, wherein a foreline and the sensor system are in fluid communication with the vacuum process chamber, the sensor system comprising a sensor manifold in fluid communication with the foreline, a sensor in fluid communication with the sensor manifold, and a gas supply line in fluid communication with the sensor manifold, the method comprising the steps of:
introducing a valving apparatus in the sensor manifold to restrict a flow of a chamber gas to the sensor;
effecting a flow of the chamber gas into the sensor manifold;
causing a sensor assistant gas to flow through the gas supply line into the sensor manifold to create a mini environment including the combined chamber and sensor assistant gases;
activating the sensor; and
testing, with the sensor, the mini environment to identify a leak in the vacuum chamber system, wherein the sensor assistant gas is configured to augment the operation of the sensor by enabling the evaluation of pressure variations and amplifying the sensitivity of the sensor.

17. The method of claim 16, wherein flowing the chamber gas comprises activating a control element.

18. The method of claim 17, wherein the control element comprises a restriction orifice, an isolation valve, a pressure controller, a pump, or a combination thereof.

19. The method of claim 17, wherein the sensor comprises a plasma assisted optical emission spectroscopy (SPOES) sensor.

20. The method of claim 17, wherein flowing the chamber gas comprises flowing the chamber gas from the foreline into the sensor manifold.

21. The method of claim 17, wherein the sensor manifold comprises an inlet portion coupled to the vacuum process chamber and an outlet portion coupled to the foreline.

22. The method of claim 21, wherein flowing the chamber gas comprises flowing the chamber gas from the vacuum process chamber into the inlet portion.

23. The method of claim 21, further comprising flowing the mini environment from the sensor manifold to the foreline.

24. The method of claim 21, further comprising flowing the chamber gas during processing in the vacuum process chamber.

25. The method for leak detection of claim 16 wherein the sensor assistant gas is $N_2$.

26. The method for leak detection of claim 16 further including the step of amplifying the sensitivity of the sensor by combining the sensor assistant gas with the chamber gases.

* * * * *